United States Patent
Saito et al.

(10) Patent No.: US 7,329,407 B2
(45) Date of Patent: Feb. 12, 2008

(54) RECOMBINANT HERPESVIRUS AND POLYVALENT VACCINE

(75) Inventors: Shuji Saito, Kawasaki (JP); Takanori Sato, Kawasaki (JP)

(73) Assignee: Zeon Corporation, Tokyo (JP)

( * ) Notice: Subject to any disclaimer, the term of this patent is extended or adjusted under 35 U.S.C. 154(b) by 345 days.

(21) Appl. No.: 11/092,838

(22) Filed: Mar. 30, 2005

(65) Prior Publication Data

US 2005/0244431 A1  Nov. 3, 2005

(30) Foreign Application Priority Data

Mar. 31, 2004  (JP) .............................. 2004-108324

(51) Int. Cl.
*A61K 39/12* (2006.01)

(52) U.S. Cl. ................. 424/199.1; 424/204.1

(58) Field of Classification Search ............. 424/199.1, 424/204.1, 201.1; 435/320.1, 69.1
See application file for complete search history.

(56) References Cited

U.S. PATENT DOCUMENTS 6,632,664 B1 * 10/2003 Saitoh et al. ............. 435/320.1

FOREIGN PATENT DOCUMENTS

| JP | 2001-188 | 1/2001 |
| WO | WO 99/18215 | * 4/1999 |

* cited by examiner

*Primary Examiner*—Ali R. Salimi
(74) *Attorney, Agent, or Firm*—Kratz, Quintos & Hanson, LLP

(57) ABSTRACT

A polyvalent vaccine for chicken coccidium-herpesvirus infections comprising as an active ingredient a recombinant herpesvirus comprising a gene encoding SEQ ID NO: 5 which is a microneme protein of a chicken coccidium protozoa or a gene in which part thereof has been substituted, deleted, or added. By administering said polyvalent vaccine into the egg, subcutaneously or intramuscularly, coccidium infections and herpesvirus infections can be prevented.

4 Claims, No Drawings

```
                         SEQUENCE LISTING

<160> NUMBER OF SEQ ID NOS: 15

<210> SEQ ID NO 1
<211> LENGTH: 22
<212> TYPE: DNA
<213> ORGANISM: Artificial
<220> FEATURE:
<223> OTHER INFORMATION: DNA Primer

<400> SEQUENCE: 1
ctttgtattc acattcaaaa tg                                            22

<210> SEQ ID NO 2
<211> LENGTH: 22
<212> TYPE: DNA
<213> ORGANISM: Artificial
<220> FEATURE:
<223> OTHER INFORMATION: DNA Primer

<400> SEQUENCE: 2
gctcactctg cttgaacctc tt                                            22

<210> SEQ ID NO 3
<211> LENGTH: 28
<212> TYPE: DNA
<213> ORGANISM: Artificial
<220> FEATURE:
<223> OTHER INFORMATION: DNA Primer

<400> SEQUENCE: 3
gaattcggca cgagctttgt attcacat                                      28

<210> SEQ ID NO 4
<211> LENGTH: 28
<212> TYPE: DNA
<213> ORGANISM: Artificial
<220> FEATURE:
<223> OTHER INFORMATION: DNA Primer

<400> SEQUENCE: 4
gtcgacacgt cgttgcgtca ctctgctt                                      28

<210> SEQ ID NO 5
<211> LENGTH: 1132
<212> TYPE: DNA
<213> ORGANISM: Eimeria tenella

<400> SEQUENCE: 5
gaattcggca cgagctttgt attcacattc aaaatggctc gagcgttgtc gctggtcgct    60
ttgggcttgc ttttttccct tcctccaagc tcagccgtta ggacgagagt cccaggcgaa   120
gatagcttct ctcctgaatc tggcgttctc agtgggacag atgcgccgga acgacgtccc   180
atcgtgcctg gactagttga aggtaactgc ggcaggctga cggttcgtaa cggcctgagc   240
gtggatgaga ccatcaaagt gaccagcgct ggatggacga agagcgaacg ggacttcatt   300
gtctcccttg ttgccgacga aacgcgcaaa gttgttcagc tgagagaatc agaaggtgca   360
tccggcgcca gtgccctgg acccgcgcca gctgaaaagc tccaagtgg ccaaggaagc    420 gctgaggagg ctcctaaagg ggaaggtgga caggagaagc cgtctgtacc cttgattgct   480
```

```
gttcgcatcc atggatctgg cggcgacaaa ggggagagcg ctccgcagtc ggctgttctg    540
ctttacggaa atgatgaaag cgagcctacg gaggttcccc tagaaacagc agctggaccg    600
accacgccac tcatggtact cattacgcag cagaacccaa aggaagtgga agtccgtgtt    660
cttgcttgga tatctacgga cgctacaact ggaaagggct cttggaaaga aaattccgtg    720
gtcgttggca gctccttgag cgggcgcgac cttaccgtga acttgagcga ctgtggacca    780
agctccctca gggtttatgg ctcggcatca gctgaccttg taactgtcaa ggagggcatg    840
tgtgaggcag acgacccaga gttgatcgcg ctgactcggc tcatacatc ggcagcttct     900 ccgctgcctg cagaggaagg agacgtagcg caggacgccc agcagagcgc aggagcccag    960
caggaagcag aagcccagga ggttggagaa ccccagcagg aagcagttgc tgcagagcaa   1020
ggaagcagcg ctgcagagag tgacactcaa cagtcatcct gaaggactgc ttaaaaatgt   1080
gcagtgttga tctggaagag gttcaagcag agtgacgcaa cgacgtgtcg ac           1132
```

<210> SEQ ID NO 6
<211> LENGTH: 39
<212> TYPE: DNA
<213> ORGANISM: Artificial
<220> FEATURE:
<223> OTHER INFORMATION: Synthetic

<400> SEQUENCE: 6

```
cagtgtcgct gcagctcagt gcatgcacgc tcattgccc                            39
```

<210> SEQ ID NO 7
<211> LENGTH: 49
<212> TYPE: DNA
<213> ORGANISM: Artificial
<220> FEATURE:
<223> OTHER INFORMATION: Synthetic

<400> SEQUENCE: 7

```
gctctagagt cgacaagctt gggggctgcg gaggaacaga gaagggaag                 49
```

<210> SEQ ID NO 8
<211> LENGTH: 20
<212> TYPE: DNA
<213> ORGANISM: Artificial
<220> FEATURE:
<223> OTHER INFORMATION: DNA Primer

<400> SEQUENCE: 8

```
gatcccctcg agggggggcc                                                 20
```

<210> SEQ ID NO 9
<211> LENGTH: 12
<212> TYPE: DNA
<213> ORGANISM: Artificial
<220> FEATURE:
<223> OTHER INFORMATION: DNA Primer

<400> SEQUENCE: 9

```
cccccctcgag gg                                                        12
```

<210> SEQ ID NO 10
<211> LENGTH: 28
<212> TYPE: DNA
<213> ORGANISM: Artificial
<220> FEATURE:
<223> OTHER INFORMATION: DNA Primer

<400> SEQUENCE: 10

-continued

```
gcgggcccta attgtttgtg tattttag                                        28

<210> SEQ ID NO 11
<211> LENGTH: 29
<212> TYPE: DNA
<213> ORGANISM: Artificial
<220> FEATURE:
<223> OTHER INFORMATION: DNA Primer

<400> SEQUENCE: 11
ttggtaccgc ttacaattta cgcgttaag                                       29

<210> SEQ ID NO 12
<211> LENGTH: 23
<212> TYPE: DNA
<213> ORGANISM: Artificial
<220> FEATURE:
<223> OTHER INFORMATION: DNA Primer

<400> SEQUENCE: 12
ctagcagtgg cagttgggaa gat                                             23

<210> SEQ ID NO 13
<211> LENGTH: 24
<212> TYPE: DNA
<213> ORGANISM: Artificial
<220> FEATURE:
<223> OTHER INFORMATION: DNA Primer

<400> SEQUENCE: 13
gttaaggcag gggaagtgat ttgt                                            24

<210> SEQ ID NO 14
<211> LENGTH: 24
<212> TYPE: DNA
<213> ORGANISM: Artificial
<220> FEATURE:
<223> OTHER INFORMATION: DNA Primer

<400> SEQUENCE: 14
ggggaagtct tccggttaag ggac                                            24

<210> SEQ ID NO 15
<211> LENGTH: 24
<212> TYPE: DNA
<213> ORGANISM: Artificial
<220> FEATURE:
<223> OTHER INFORMATION: DNA Primer

<400> SEQUENCE: 15
ggtgcaattc gtaagaccga tggg                                            24
```

RECOMBINANT HERPESVIRUS AND POLYVALENT VACCINE

FIELD OF INVENTION

The present invention relates to a recombinant herpesvirus vaccine for chickens to prevent avian coccidium infections.

BACKGROUND ART

Chicken coccidiosis is one of the most feared parasite infections in the poultry industry, and it can cause the death of about 50% of the affected individuals within a few days after infection. In chronic infection, diarrhea, emaciation, anastasia are noted, causing an enormous damage to the breeding of broilers in the poultry industry. In particular, chicks in the stage of young chicks and middle chicks, important periods for meat chickens, are vulnerable to the disease, and once infection has occurred, it is very difficult to root coccidium out. Currently, though antibiotics and chemical synthetic agents play important roles as preventive measures against this disease, the need to administer them prior to the onset of the disease and in succession leads to higher cost in production and side effects, due to successive use are concerned.

Furthermore, in order to solve these problems, various live vaccines have been developed. Some of them are coccidia with moderate pathogenicity, which per se form significant lesions. Recently, a vaccine that uses precocious strains and that is effective to some extent was developed. However, as there is residual pathogenicity in this vaccine too, there remains a concern over the mutation of the vaccine strain to the wild type strain. For the inoculation of a vaccine strain, the inoculation schedule together with other vaccines must be taken into account and, as the use of antibacterial agents is limited, it is feared that other infections may occure.

Concerning about side effects by these drugs and live vaccines, persistent efforts have been made to search for protective antigens for coccidiosis in order to develop safer component vaccines and recombinant vector vaccines, but there are no reports that indicate the achievement of sufficient effects.

Currently, many of the coccidium antigens have been analyzed to the level of sequence analysis, and the antigens have been localized. A lot of genes of antigen proteins have been found such as Ta4, an oocyst antigen of *E. tenella* (U.S. Pat. No. 5,028,694) ns GX3262 (U.S. Pat. No. 5,122,471), Mzp5-7 (U.S. Pat. No. 5,403,581), EtMIC5 (Mol. Biochem. Parasitol., 15:91-102, 2000), EtMIC2 (Mol. Biochem. Parasitol., 79:195-206, 1996), cMZ8 of *E. acervulina* (Infect. Immun., 57:2434-2440, 1989), and EAMZ 250 (Immunology, 71:127-132, 1990). Though some of these antigen genes have been integrated into fowlpox virus and vaccinia virus (U.S. Pat. No. 5,814,320, U.S. Pat. No. 5,403,581), they have not been confirmed to give effective vaccines.

This results from the fact that antibody alone cannot protect against protozoan infections, in addition to the difference in genome size of virus and protozoa or the difference in the morphology in the infected organism.

DISCLOSURE OF INVENTION

After intensive and extensive research to obtain recombinant vaccines under the current state of art, the present inventors have found that by integrating the gene encoding the microneme protein of *Eimeria tenella*, cell-mediated immunity can be conferred in addition to antibody formation exhibiting a high protective effect against coccidium infection, and thereby have completed the present invention.

Thus, in accordance with the present invention, there is provided a recombinant herpesvirus comprising a gene encoding SEQ ID NO: 5 which is a microneme protein of the chicken coccidium protozoa or a gene in which part thereof has been substituted, deleted, or added. Said gene is positioned under the control of an altered β-actin promoter that can exhibit a promoter activity in avian herpesviruses.

Also, in accordance with the present invention, there is provided a polyvalent vaccine for chicken coccidium—herpesvirus infections.

Furthermore, there is provided a method of inoculating a polyvalent vaccine (referred to hereinafter as a polyvalent vaccine for chicken coccidium—herpesvirus infections, or simply a polyvalent vaccine) comprising inoculating a said polyvalent vaccine into the egg, subcutaneously, or intramuscularly.

In accordance with the present invention, there is provided a recombinant vector comprising a gene encoding SEQ ID NO: 5 which is a microneme protein of the chicken coccidium protozoa or a gene in which part thereof has been substituted, deleted, or added. This recombinant vector is used to construct the recombinant herpesvirus of the present invention.

BEST MODE FOR CARRYING OUT THE INVENTION

The present invention will now be explained in further detail below.

The recombinant herpesvirus of the present invention has a gene encoding SEQ ID NO: 5 which is a microneme protein of the chicken coccidium protozoa or a gene in which part thereof has been substituted, deleted, or added.

The gene encoding SEQ ID NO: 5 which is a microneme protein of the chicken coccidium protozoa is the EtMIC2 gene, and has the base sequence as set forth in SEQ ID NO: 5. Also, in accordance with the present invention, this EtMIC2 gene may undergo mutation so that part (one or multiple bases) of the base sequence as set forth in SEQ ID NO: 5 has been substituted, deleted, or added.

In accordance with the present invention described hereinbelow, unless otherwise specified, "EtMIC2 gene" means a gene encoding SEQ ID NO: 5, or a gene in which part thereof has been substituted, deleted, or added.

Herpesviruses that infect avians are preferred, and preferably Marek's disease virus (sometimes referred to hereinafter as MDV) or infectious laryngotracheitis virus (referred to hereinafter as ILTV) is selected.

Marek's disease virus comes in three types: type 1, 2 and 3, and any type may be selected for use in the present invention. As the Marek's disease virus, there can be mentioned those obtained naturally or from ATCC etc. free of charge, and specifically non-pathogenic ones are preferred. As examples of such viruses, there can be illustrated the CVI988 (Rispens) strain for Marek's disease virus type 1, SB-1 strain for Marek's disease virus type 2, and FC126 (ATCC VR-584B), PB-THV1, H-2, YT-7, YTHV-1, HPRS-26 and the like for Marek's disease virus type 3 (turkey herpesvirus; referred to hereinafter as HVT). Specifically Marek's disease virus type 3 is preferred.

As ILTV, there can be illustrated the NS-175 strain (The List of Livestock Health Organisms VA0204, Japanese Association of Veterinary Biologics), the CE strain (Kouda, Azabu Veterinary College Research Report, 31:133-202, 1976), the SA-2 strain (Johnson et al., Arch. Virol., 119: 181-198, 1991), the attenuated field isolate 623 strain (Keeler et al., Avian Diseases, 35:920-929, 1991), and the USDA challenge strain (Poulsen et al., J. General. Virol., 78:2945-2951, 1997).

There are no limitations on integrating the EtMIC2 gene into herpesvirus, and there can be used a conventional recombinant technology in which the EtMIC2 gene is inserted into a genome region non-essential for viral growth of a recombinant vector, and homologous recombination is carried out between said recombinant vector and the herpesvirus.

The EtMIC2 gene is preferably positioned under control of a promoter. Furthermore, it is also preferred that a signal sequence such as a poly A addition signal is positioned downstream of the WtMIC2 gene.

As vectors, there can be mentioned plasmids, cosmids and phages that are commonly used in gene recombinant technology.

As plasmids, there can be mentioned commercially available plasmids such as pBR322, pBR325, pUC7, pUC8 and pUC18; as cosmids, there can be mentioned commercially available phages such as pJB8 and pHC79, and; as phages, there can be mentioned commercially available phages such as λ phage and M13mp18.

The genome regions non-essential for herpesvirus include a known region (a known non-essential region) used in recombinant HVT, a genome region homologous thereto in other herpesviruses, and the like.

As specific examples of known non-essential regions, there can be illustrated the UL43 gene described in WO89/01040, the US2 gene described in WO93/25665 (U.S. Pat. No. 5,928,648), and the region between open reading frames of UL44 to UL46 described in WO99/18215 (U.S. Pat. No. 6,632,664), and the most preferred region is the region between the open reading frames of UL45 and UL46.

These known non-essential regions are not limiting, and new non-essential regions may be found. Methods of finding new non-essential regions include, but not limited to, a common method such as described below. Thus, a genomic DNA fragment of HVT is cloned, a restriction enzyme is mapped, a recombinant plasmid in which the marker gene together with the promoter has been integrated into a suitable restriction enzyme site, and it is investigated whether a stable recombinant herpesvirus can be obtained both in vitro and in vivo using the method of creating a common avian herpesviruses described below.

With regard to promoter genes for use in the efficient expression of the EtMIC2 gene, those that function as promoters in the cells infected with the recombinant herpesvirus of the present invention are expected to be effective, and there can be preferably used those promoters having high activity in chickens, such as the thymidine kinase promoters of herpesvirus (Ross et al., J. Gen. Virol. 74:371-377, 1993), the gB protein promoter of herpes virus of turkey (HVT) and Marek's disease virus (MDV) type 1 (Ross et al., J. Gen. Virol. 74:371-377, 1993), the IE promoter of human cytomegalovirus (HCMV) (Stinski et al., J. Virol. 55:431-441, 1985), the SV40 promoter (Gunning et al., Proc. Natl. Acad. Sci. USA 84:4831-4835, 1987), the human β actin promoter (Gunning et al., Proc. Natl. Acad. Sci. USA 84:4831-4835, 1987), chicken β actin promoter (Kost et al., Nucleic Acids Res., 11:8287-8301, 1983), the LTR promoter of Rous sarcoma virus (RSV) (Greuel et al., Virology 177:33-43, 1990), and the Pec promoter (Japanese Unexamined Patent Publication (Kokai) No. 2001-000188).

Among them, it is preferred to use the β actin promoter derived from chicken cells having a very high activity in herpesvirus, and modified versions thereof.

By adding an enhancer, in addition to a promoter, a more efficient expression can be expected (Stinski et al., J. Virol. 55:431-441, 1985). As enhancers, there can be mentioned part of cytomegalovirus-derived promoters, and the position relative to the inserted gene is not usually limited. As promoters of this type, there can be illustrated the Pec promoter described in Japanese Unexamined Patent Publication (Kokai) No. 2001-000188.

As a method of creating a recombinant herpesvirus, there can be mentioned the following method:

(1) Firstly, a plasmid in which a genomic DNA fragment of a herpesvirus containing the above-mentioned non-essential region is obtained, and then the EtMIC2 gene is inserted into said non-essential region of this plasmid to construct a recombinant plasmid. Thereupon, it is more preferred to insert a plasmid in which a promoter has been added upstream of the 5'-end and a poly A signal downstream of the 3'-end and which has been linked to the EtMIC2 gene. (2) The constructed recombinant plasmid is introduced into herpesvirus-infected CEF cells. Alternatively, the recombinant plasmid is introduced into CEF cells together with the infectious genomic DNA prepared from HVT. These introduction methods may be commonly used ones such as electroporation. (3) CEF cells that have introduced the recombinant plasmids therein are plated on a culture dish, and are cultured until the plaques become fully enlarged. (4) From the plaques in which both the recombinant virus and the wild type virus are present, the objective recombinant virus is purified. As the method of purification, there can be illustrated, but it is not limited to, a method in which CEF cells in which plaques developed are diluted as appropriate, plated on a 96-well plate, and then plaques of the recombinant virus that expresses the EtMIC2 protein are detected using, as a primary antibody, a monoclonal antibody or a polyclonal antibody against the protein (i.e. the EtMIC2 protein; a kind of microneme protein) expressed by the EtMIC2 gene.

Though the recombinant herpesvirus of the present invention may be used as a vaccine for chicken coccidiosis since it has the gene, EtMIC2, that encodes the microneme protein of *Eimeria tenella*, the causative protozoa of chicken coccidiosis, it can also provide an effective bivalent vaccine for herpesvirus infections as well as chicken coccidiosis.

The vaccine having the recombinant herpesvirus of the present invention as the main ingredient may contain cells or components of the culture medium. The components other than the recombinant virus are not specifically limited and may be a stabilizer for storage, a buffer etc. that are physiologically inert. Furthermore, as components other than the recombinant virus, other recombinant or non-recombinant viruses may be mixed. Specifically, there can be illustrated a case in which, when the recombinant herpesvirus is HVT, a vaccine strain such as MDV-1 or MDV-2 may be mixed with the recombinant HVT of the present invention. The recombinant HVT is a coccidium vaccine per se and serves simultaneously as a virus for Marek's disease.

It can also be mixed with recombinant viruses in which an antigen gene derived from another pathogen has been inserted.

As the method of preparing the bivalent vaccine of the present invention, there can be mentioned, but not limited to, the following method. After the recombinant herpesvirus of the present invention is infected to CEF cells in which said virus can propagate and has been propagated, the infected cells are scraped with a scraper or trypsin, and subjected to centrifugation to separate the cells from the supernatant. The cells obtained are suspended in a culture medium containing 10% dimethyl sulfoxide (DMSO) and stored in liquid nitrogen.

The method of administering the bivalent vaccine of the present invention to chickens is not specifically limited, and a common method used for herpesvirus vaccines may be used. Thus, it is dissolved in a suitable amount of a phosphate buffer or solution to a concentration of $10\text{-}10^5$ PFU/dose, preferably $10^2\text{-}10^4$ PFU/dose, which is administered subcutaneously into the neck of a one-day old chick, intramuscularly into the femoral region, the pectoralis major, or an egg before hatching by injection or using an inoculation device.

EXAMPLES

The plasmid of the present invention was constructed using a standard molecular biology technique that is described, unless otherwise specified, in Molecular Cloning: A Laboratory Manual, 2nd Edition (Cold Spring Harbor Laboratory, Cold Spring Harbor, N.Y. 1989). The restriction enzyme fragments were purified from agarose gel using he QIAquick Gel Extraction Kit (QUIAGEN, Cat. No. #28704).

Example 1

Isolation of EtMIC2 DNA

Sporozoites of a *E. tenella* USA strain were dissolved according to a standard method in a detergent, and then mRNA was purified by the Olig(dT) cellulose column (Fast-Track, Invitrogen). The double stranded DNA was synthesized using ZAP-cDNA (Stratagene) and then cloned into the Uni-ZAP XR vector and packaged into the X phage (Gigapack II, Stratagene). After amplifying the thus prepared primary library, it was infected to *E. coli*, and phages into which the EtMIC2 gene has been inserted were selected by plaque hybridization. Specifically, from the EtMIC2 gene sequence (Jianlin, J. and Jinshu, J. Accession No. AF111839) registered in the NCBI Gene Bank, EtMIC2-F (SEQ ID NO: 1), two synthetic DNAs of a sequence of a segment corresponding to the N-terminal end of the EtMIC2 gene, and EtMIC2-R (SEQ ID NO: 2), a sequence of a segment corresponding to the C-terminal end of the EtMIC2 gene, were prepared, and were subjected to labelling with digoxigenin (DIG) using the PCR DIG Probe Synthesis Kit (Boehringer Mannheim, Cat. No. 1636 090).

Using these labelled probes, a plaque hybridization was carried out according to a standard method. For the detection of λ phage plaques to which the above labelled DNA hybridizes, an alkaline phosphatase-labelled anti-DIG antibody diluted 1000-fold in PBS for probe detection was used and, by allowing color development of the developing reagent (NBT/BCIP) (Boehringer Mannheim, Cat. No. 1681451), probe-hybridized plaques only were colored blue purple. By screening about 20,000 plaques, two plaques to which the two probes hybridized were selected. Furthermore, phages that formed reactive plaques were subjected to PCR cloning with non-labelled EtMIC2-F and EtMIC2-R as synthetic DNA primers. As a result, DNA of about 1 kbp was cloned. In order to further clone this DNA into the pPCR-script vector, synthetic DNAs of SEQ ID NO: 3 and SEQ ID NO: 4 were constructed, PCR was further carried out and, after cleaving with SalI-XhoI, it was cloned into a pPCR-script vector to obtain a plasmid pPCR-EtMIC2.

By the analysis of sequence of the plasmid-inserted fragment using the DNA analysis system (Beckman, CEQ2000XL), the cloned fragment (SEQ ID NO: 5) was identical with the EtMIC2 gene sequence (Jianlin, J. and Jinshu, J. Accession No. AF111839) registered in the NCBI Gene Bank except the newly added restriction enzyme cleavage point.

Example 2

Construction of a Recombinant Plasmid (p45BacEtMIC2)

2-1 Isolation of Chicken β-Actin Promoter

Using the primer PrBac1 (SEQ ID NO: 6) and the primer PrBac 2 (SEQ ID NO: 7) with the genomic DNA of chick embryo fibroblast (CEF) using as templates, a DNA fragment (about 1.5 Kbp) containing a chicken β-actin promoter was obtained by PCR. A DNA fragment excised by double digestion of this DNA with restriction enzymes PstI and XbaI was cloned into a plasmid pUC18, and the base sequence of this DNA fragment was analyzed using the above-mentioned DNA sequencer. It was confirmed to be a chicken β-actin promoter.

2-2 Construction of a Plasmid pGIBacpA

The plasmid pGIMCSpolyASfi (2,773 bp) described in WO99/18215 was cleaved with restriction enzymes BamHI and ApaI, to which a double stranded DNA adaptor prepared by annealing a synthetic oligonucleotide Ad-B-A-U (SEQ ID NO: 8) and a synthetic oligonucleotide Ad-B-A-L (SEQ ID NO: 9) was inserted to construct a plasmid pGIMCS2 (2,765 bp).

Then, the chicken β-actin promoter (1,523 bp) in 2-1 excised by double digestion with restriction enzymes PstI and XbaI and a plasmid fragment obtained by cleaving pGIMCS2 similarly with restriction enzymes PstI and XbaI were ligated to construct pGIBac (4,272 bp).

Using the primer PolyA-F (SEQ ID NO: 10) and the primer PolyA-R (SEQ ID NO: 11) with the plasmid PBK-CMV (manufactured by STRATAGENE, Cat. No. 212209) as a template, PCR was carried out to amplify a DNA fragment (334 bp) of the polyA signal of SV40, and this was cleaved with restriction enzymes ApaI and KpnI to obtain a DNA fragment (324 bp), which was inserted to pGIBac also doubly cleaved with ApaI and KpnI to construct pGIBacpA (4,584 bp).

2-3 Construction of pNZ45/46BacpolyA pGIBacpA constructed as above was cleaved with a restriction enzyme BglI and the DNA fragment was separated by an agarose gel electrophoresis to harvest a 1,931 bp DNA fragment from the agarose gel. The harvested DNA fragment was inserted to a plasmid pNZ45/46Sfi (full length 5,493 bp) described in WO99/18215 cleaved with a restriction enzyme SfiI to construct pNZ45/46BacpolyA (7,424 bp).

2-4 Construction of p45BacEtMIC2

In order to construct a plasmid for preparing a recombinant HVT containing the EtMIC2 gene, an about 1132 bp fragment obtained by cleaving pPCR-EtMIC2 with BamHI and SalI and a fragment obtained by cleaving pNZ45/46BacpolyA with BamHI and SalI were ligated to construct pNZ45BacEtMIC2 (8461 bp).

Incidentally, pNZ45/46BacpolyA as used herein is a plasmid for HVT recombination that was assembled to express an inserted antigen gene with a chicken β-actin promoter.

Example 3

Construction and Purification of rHVT/EtMIC2

According to a method by Morgan et al. (Avian Diseases 34:345-351, 1990), the DNA of the parent HVT strain was prepared, which was inserted to CEF cells together with the plasmid p45BacEtMIC2 constructed in Example 2 using electroporation, and the recombinant HVT was purified using an antibody against EtMIC2 or an antibody against *E. tenella*. The specific procedures thereof are as follows.

p45BacEtMIC2 (5 μg) and HVT genomic DNA (25 μg) were suspended into 100 μl of saline G (0.14 M sodium chloride, 0.5 mM potassium chloride, 1.1 mM disodium hydrogen phosphate, 1.5 mM monosodium dihydrogen phosphate, 0.5 mM magnesium chloride hexahydrate, 0.011% glucose). $2 \times 10^6$ chick embryo fibroblasts (CEF) were suspended into 0.7 ml of saline G, which was added to the above DNA solution to effect gene transduction at room temperature using the Gene Pulser (Bio-Rad) under the condition of 25 μF, 1.2 kV, and 0.4 msec. After the cells were allowed to stand at room temperature for 10 minutes, Leibovit'z L-15 containing 4% bovine serum: McCoy's 5A Medium (1:1) (both manufactured by GIBCO BRL, Cat. No. 41300-039, 21500-061) (referred to hereinafter as LM(+) medium) was added, and cultured in an cell culture dish with a diameter of 60 mm in a 37° C., 5% $CO_2$ incubator for 6 days. The cells were diluted as appropriate, and mixed with CEF suspended in the LM(+) medium, aliquoted in a 96-well culture plate, and cultured until plaques are formed.

Cells in each well were trypsinized, and after adding fresh CEF cells, they were transferred to wells of two 96-well culture plates. Replica plates thus prepared were cultured until plaques have appeared. Then, cells in one of the plates were fixed in methanol, and by an antigen-antibody reaction using a polyclonal antibody against the EtMIC2 protein as a primary antibody, it was confirmed whether a recombinant HVT that expresses the EtMIC2 protein is present or not. From the replica corresponding to the well in which recombinant HVT was confirmed, cells were harvested, diluted, mixed with fresh CEF cells suspended in the LM(+) medium, aliquoted in a 96-well plate, and cultured. This process of dilution, replica preparation and recombinant HVT confirmation was repeated until all plaques derived from one well are confirmed to be 100% recombinant HVT. After growing this recombinant HVT to about $10^5$ PFU with CEF, it was subjected to an ultrasonic disruption treatment, and the centrifuge supernatant was infected with CEF cells in a 96-well plate. After culturing for one week, this procedure was repeated again until the recombinant HVT became 100%. The recombinant HVT virus thus purified was termed rHVT/EtMIC2.

Example 4

Confirmation of Stability of rHVT/EtMIC2

3-1 Southern Hybridization

The purified recombinant HVT virus was cultured in two culture plates with a diameter of 150 mm together with CEF cells until plaques appeared throughout the entire surface, and the infected cells were scraped with a scraper followed by centrifuge (250 G, 5 minutes) to harvest the infected cells. The cells obtained were washed in PBS and then resuspended in 1.2 ml of PBS, to which 0.8 ml of lysis buffer (1.25% Triton X-100, 250 mM 2-ME, 50 mM EDTA in PBS) was added, and vortexed (for 30 seconds) to solubilize the cells. The cell debris were removed by centrifugation (1,500 G, 5 minutes), and the supernatant was transferred into an Eppendorf tube, which was centrifuged at 15,000 G for 20 minutes at 22° C. to collect the virus. One ml of 12.5 mM Tris-HCl (pH 7.5) was added thereto, and 4 μl of the nuclease mixture (0.25 mg/ml DNAaseI, 0.25 mg/ml RNaseA, 150 mM sodium chloride) and allowed to stand at 37° C. for 30 minutes. Thereafter, 25 μl of 500 mM EDTA, 125 μl of 10% SDS, 87 μl of $H_2O$, 12.5 μl of 10 mg/ml Proteinase K and 0.5 μl of 2-mercaptoethanol were added, and was allowed to stand at 55° C. for 30 minutes. The solution was extracted twice with phenol/chloroform.

To the aqueous phase was added 16 μl of 5M sodium chloride, and 2.5 volume part of 100% ethanol (cooled to −20° C.) was added to form precipitate, and the precipitate (DNA) obtained by centrifugation was washed in 70% ethanol, centrifuged again to precipitate, which was then dried, and dissolved in 50 μl of TE buffer (10 mM Tris-HCl, pH 8.0, 1 mM EDTA).

The viral DNA thus collected was cleaved with XhoI and EcoRV, subjected to electrophoresis on a 0.8% agarose gel, and the restriction-cleaved DNA fragments were blotted to a nylon membrane for Southern hybridization. As probes, two DIG-labelled DNA probes were prepared using the reagent of "PCR DIG Probe Synthesis Kit" (ROCHE DIAGNOSTICS, Cat. No. 1636090). The DNA probes are a probe (referred to hereinafter as EtMIC2 probe) in the EtMIC2 DNA region and a HVT genome region (referred to hereinafter as 45/46 probe) at the insertion site of a foreign gene. The former probe was prepared using two primers EtMIC2-F2 (SEQ ID NO: 12) and EtMIC2-R2 (SEQ ID NO: 13) and a plasmid p45/46EtMIC2 as a template, and the latter was prepared using two primers 45/46-F (SEQ ID NO: 14) and 45/46-R (SEQ ID NO: 15) and a plasmid pNZ45/46Sfi as a template.

As a result of Southern hybridization using these two probes, the EtMIC2 probe hybridized to 2004 bp and 631 bp bands, while the 45/46 probe hybridized to 2004 bp and 840 bp bands. This result indicated that both probes yielded bands as expected, confirming that the recombinant virus is a correct recombinant as designed.

Example 5

Confirmation of Stability of the Recombinant HVT Genome Structure (in vitro)

For recombinant virus obtained by passages of recombinant HVT for ten times in CEF cells, Southern blotting was carried out similarly to Example 3-1, and it was confirmed that the recombinant virus after passages for ten generations had the correct recombinant virus, confirming that it is a stable recombinant.

Example 6

Confirmation of Stability of the Recombinant

HVT genome structure (in vivo)

rHVT/EtMIC2 at 3000 PFU was subcutaneously inoculated at the back of one-day old commercially available chicks and SPF chickens, bred for five weeks, and at 3, 4, and 5 week-old, peripheral blood was collected from veins under the wing, and virus was isolated from lymphocytes in the peripheral blood. The isolation of the lymphocytes from the peripheral blood was carried out as follow.

0.5 ml of 100 U/ml heparin solution was first taken in a 2.5 ml syringe, and then 2 ml of blood was taken into the syringe from the wing, and the mixture was layered on 5 ml of Ficoll-Paque (Amersham-Pharmacia) in 15 ml Falcon tubes. By centrifuging at 550 G for 20 minutes, peripheral blood lymphocytes appeared as bands 15 at the interface between the Ficoll-Paque and the serum components. This part was aspirated using a Pasteur pipet, and was mixed with CEF that had been plated in a 9 cm petri dish, and cultured for seven days. Furthermore, this CEF was passaged twice to investigate the appearance of virus plaques. When plaques appeared twice during the passaging, it was judged that viruses could be separated from lymphocytes. The result is shown in Table 1.

TABLE 1

|  | rHVT/EtMIC2 | | FC126 | | Non-inoculated chickens MA+ |
| --- | --- | --- | --- | --- | --- |
|  | Commercially available chickens | SPF | Commercially available chickens | SPF |  |
| 3 week old** | 2/2* | N/A | 2/2 | 1/1 | N/A |
| 4 week old | 3/3 | 2/2 | 3/3 | 2/2 | 0/2 |
| 5 week old | 3/3 | 2/2 | 1/3 | N/A | 0/2 |

*No. of chickens for which virus was separated/No. of chickens for which lymphocytes were collected
**weeks of age For recombinant HVT also, virus could be separated from the peripheral blood lymphocytes at any period from 3-5 week-old as in the parent strain. Plaques of the virus that could be separated were differently colored as in Example 2 so as to test the expression of EtMIC2 protein, and as a result, it was found that all the separated plaques expressed the EtMIC2 protein. From this result, it was confirmed that recombinant HVT is stable in vivo as well.

Example 7

Confirmation of Expression of the Recombinant HVT Gene 7-1 Immunofluorescence Technique The above recombinant HVT-infected cells, that were cultured in a chamber slide for tissue culture, were cultured at 37° C. together with CEF until plaques appeared, and fixed in cold acetone. As the primary antibody used for the detection of the antigen expressed, serum from a purified EtMIC2 protein-immunized rabbit was used for the detection of the EtMIC2 protein, and anti-Newcastle disease virus chicken serum for non-reactive control serum and a monoclonal antibody R63 against VP2 protein of infectious bursal disease were used. Each serum and monoclonal antibody were diluted 500-fold in PBS for use. The reaction time was about one hour at room temperature at a moisture of 100%, and after washing three times in PBS, was reacted at room temperature for about one hour with a solution in which a fluorescence indicator (FITC)-bound anti-chicken immunoglobulin or anti-rabbit IgG was diluted 100-fold in PBS. Then, after washing three times in PBS, it was examined by a microscope under a fluorescent excitation light to investigate reactivity. As the control virus, cells infected with the HVT parent strain FC126 as the subject virus were used. The result is shown in Table 2.

TABLE 2

| Infected virus | Anti-EtMIC2 rabbit serum | Anti-NDV chicken serum | Anti-VP2 Mab (R63) | PBS |
| --- | --- | --- | --- | --- |
| rHVT/EtMIC2 | + | − | − | − |
| FC126 | − | − | − | − |
| Non-infected cells | − | − | − | − |

+: Reacted,
−: Not reacted.

As can be seen from Table 2, the recombinant HVT was found to express the inserted EtMIC2 gene.

7-2 Western Blotting

After culturing CEF infected with recombinant HVT at m.o.i =0.1 for 72 hours, they were solubilized with a SDS-GEL loading buffer. As a control, CEF not infected with the virus or the parent strain FC126 infected with the same m.o.i=0.1 for 72 hours were similarly solubilized. These samples were subjected to a common SDS-PAGE under a denatured reduced condition. Then, migrating proteins were transferred from the SDS gel to a PVDF membrane (Immobilon-P, Millipore). After transferring, the PVDF membrane was blocked with PBS containing 1% skim milk at room temperature for 1 hour. Then, it was incubated at room temperature with anti-F rabbit serum diluted 500-fold in PBS, washed three times in PBS, and then incubated for 1 hour with a 500-fold diluted biotinylated anti-rabbit antibody (derived from goat serum). After washing three times in PBS, it was incubated with an avidin-alkaline phosphatase complex for 1 hour, washed three times in PBS and once in TBS, and color was developed with BCIP-NBT, a substrate for alkaline phosphatase. As a result, the presence of the MIC2 protein was only confirmed in the recombinant rHVT/EtMIC2-infected cells at the predicted size of molecular weight 47 KDa.

Example 8

Experiment on Protection Against Animal Coccidium Infection

In order to evaluate the effect of the HVT recombinant vaccine obtained in Example 3 on coccidium, a coccidium-infection protection experiment was carried out.

To twelve birds per group of one day-old SPF chicks for testing (LineM, Nippon Institute for Biological Science) was inoculated recombinant HVT to 3000 PFU/100 µl/chicken subcutaneously at the back using a syringe needle having a 20 G diameter. The triple combined live vaccine TAM (Nippon Institute for Biological Science) for coccidiosis was inoculated to four-days old according to a regimen, and the negative control received no inoculation. Thirty-four days (35-day old) after the inoculation of the recombinant HVT or the triple combined live vaccine, 380 sporulated oocysts of Rt7 strain, a field isolate of *E. tenella*, were challenged to the crop of chicks by a single-dose forced per os. The following items were observed or measured. The observation period was up to 8 days after challenge. The excretion of oocysts was confirmed every day from day 5 after challenge and after by the presence of oocysts excretion by the saturated saline suspension method. When oocysts were detected, the number (OG) of oocysts per g of feces was measured by the chromate acid mixture method. For intestinal lesions, all chickens were killed on day 8 after challenge for autopsy, and the degree of visual lesion of caecum was observed. The degree of lesion was recorded according to Johnson & Reid method (Johnson, J. and Reid, M., Experimental Parasitology 28:30-36, 1970) in five stages from 0 (normal) to +4 (the most severe). Significance test of intestinal lesion was carried out by the Mann-Whitney U test in which each vaccine inoculation group and the non-immunized control group were compared. The result is shown in Table 3.

TABLE 3

| Treatment group | Inoculated dose | Number of chickens | OPG (×10³) Day 5 | Day 6 | Day 7 | Feces appearance[2]* | Mean lesion score[3]* (p)[4]* |
|---|---|---|---|---|---|---|---|
| Non-inoculated, non-infected group | – | 10 | – | – | – | – | 0 |
| Non-inoculated, infected group | – | 11 | 8.0 | 1136 | 59.2 | ++ | 2.27 ± 0.19 |
| Live vaccine inoculated group | Regimen | 11 | – | 108.8 | 1.8 | + | 1.45 ± 0.21 (0.008) |
| rHVT/EtMIC2 inoculated group | 3000[1]* | 12 | 0.3 | 464.0 | 48.0 | + | 1.50 ± 0.23 (0.017) |

[1]*PFU
[2]*Appearance of feces on day 6 after challenge, +: abnormal feces not greater than 25%, ++: abnormal feces 25-50%
[3]*0 = normal, 1 = mild, 2 = moderate, 3 = severe, 4 = most severe
[4]*Result of Mann-Whiteney U test (comparison with the non-inoculation group)

As shown in Table 3, the chicken group that received recombinant HVT/EtMIC2 had a significantly smaller number of excreted oocysts as compared to the non-inoculation group against the highly toxic *E. tenella* challenge, and caecum lesion was almost equal to a commercially available vaccine, and significantly low as compared to the non-inoculated challenged group, indicating a notable activity of protecting against coccidium infection.

Example 9

Isolation of rHVT From Peripheral Blood Lymphocytes of rHVT-Inoculated Chickens rHVT/EtMIC2 at 3000 PFU was subcutaneously inoculated at the back of one-day old SPF chicks, the chickens were bred for 30 weeks, and peripheral blood was collected from veins under the wing every two weeks, and virus was separated from peripheral blood lymphocytes. Separation of lymphocytes from peripheral blood was carried out in the same manner as in Example 6.

As a result, virus was separated from lymphocytes of all chickens that received recombinant HVT. The expression of the EtMIC2 protein was investigated in the same manner as in Example 7 with a result that all the viruses expressed the EtMIC2 protein at the same level as that during purification of recombinant HVT. Also, when the virus isolated after breeding for 30 weeks was subjected to Southern blotting in the same manner as in Example 3 to examine the stability of virus, both of the inserted genes and insertion sites had the same structure as the virus at the time of inoculation. This indicated that the present recombinant HVT is structurally stable for a long time in chickens and stably expresses the antigen protein.

Example 10

Experiment on Protection Against Marek's Disease Infection

In order to evaluate the effect of the HVT recombinant vaccine obtained in Example 3 on Marek's disease, a Marek's disease-infection protection experiment was carried out. To twelve birds per group of one day-old SPF chicks for testing (LineM, Nippon Institute for Biological Science) was inoculated recombinant HVT to 3000 PFU/100 μl/chicken subcutaneously at the back using a syringe needle having a 20 G diameter. Also, 3000 PFU of a HVT vaccine, FC126, was inoculated in a similar manner. All the other groups of similar chicks were not inoculated with vaccine. To all 6-day old chicks except the non-inoculation challenge group, the Md5 strain, an extremely highly toxic Marek's disease challenge strain at 500 PFU was challenged subcutaneously. Deaths resulting from Marek's disease during the test were recorded, and at the time of completion of the 8-week long test, visual lesion and tumor typical for Marek's disease were examined. The result of the test is shown in Table 4.

TABLE 4

| Treatment group | Inoculated dose | Number of chickens | Number of deaths | Number of Marek's disease | % protection rate |
|---|---|---|---|---|---|
| Non-inoculated, non-challenged group | — | 12 | 0 | 0 | |
| Non-inoculated, challenged group | — | 12 | 10 | 12 | 100 |
| FC126 inoculated group | 3000[1]* | 12 | 0 | 2 | 83 |
| rHVT/EtMIC2 inoculated group | 3000 | 12 | 0 | 1 | 92 |

[1]*PFU

In the non-inoculated challenged group, a significant number of chicks died due to Marek's disease prior to the completion of the test. On the other hand, the vaccine inoculation group and the FC126 inoculation group were not only protected from death due to Marek's disease but exhibited no typical lesions, indicating a favorable vaccine effect.

From the foregoing, it can be seen that the recombinant herpesvirus of the present invention could provide a very effective vaccine against the infection by coccidium and Marek's disease virus, one of the herpesviruses.

The invention claimed is:

1. A recombinant herpesvirus comprising a gene encoding SEQ ID NO: 5, which is a microneme protein of a chicken coccidium protozoa, or a gene that has the sequence of SEQ ID NO: 5 in which part thereof has been substituted, deleted, or added.

2. A polyvalent vaccine comprising the recombinant herpesvirus according to claim 1 as an active ingredient for preventing chicken coccidium infections and herpesvirus infections.

3. A method of inoculating the polyvalent vaccine according to claim 2 for preventing chicken coccidium infections and herpesvirus infections wherein said polyvalent vaccine is inoculated into the egg, subcutaneously or intramuscularly.

4. A recombinant vector comprising a gene encoding SEQ ID NO: 5 which is a microneme protein of a chicken coccidium protozoa or a gene in which part thereof has been substituted, deleted, or added.

* * * * *